United States Patent [19]
Ragonesi et al.

[11] Patent Number: 5,400,617
[45] Date of Patent: Mar. 28, 1995

[54] DEVICE FOR THE LOCAL COOLING OF HUMAN BODY PARTS

[76] Inventors: Roberto Ragonesi; Silvana Bianchi, both of Via G. Matteotti, 1, 50012 Bagno A Ripoli (Prov. of Florence), Italy

[21] Appl. No.: 140,399

[22] Filed: Oct. 25, 1993

[30] Foreign Application Priority Data

Jul. 15, 1993 [IT] Italy ............... MI 93 U 000573 U

[51] Int. Cl.⁶ .................................................. F25D 3/08
[52] U.S. Cl. .................................... 62/530; 607/109; 165/10
[58] Field of Search ................. 62/530; 607/109, 112, 607/114; 165/10

[56] References Cited
U.S. PATENT DOCUMENTS

| | | | |
|---|---|---|---|
| 750,104 | 1/1904 | Eggers | 607/109 |
| 1,610,712 | 12/1926 | Schweinert | 607/109 |
| 2,250,840 | 7/1941 | Pomeranz | 607/109 |
| 4,908,248 | 3/1990 | Nabashima et al. | 62/530 |
| 4,910,978 | 3/1990 | Gordon et al. | 62/530 |
| 5,005,374 | 4/1991 | Spitler | 62/530 |

*Primary Examiner*—A. Michael Chambers
*Attorney, Agent, or Firm*—Oliff & Berridge

[57] ABSTRACT

Device for the local cooling of human body parts consisting of:
a) a sheath;
b) cooling means contained in said sheath;
c) a flexible leaf contained also in said sheath, apt to adhere said sheath and said cooling means to the human part to cool.

12 Claims, 1 Drawing Sheet

DEVICE FOR THE LOCAL COOLING OF HUMAN BODY PARTS

FIELD OF THE INVENTION

The present invention relates to a new device for the local cooling of human body parts.

It is particularly suitable for athletes who need a local cooling of body parts (especially neck and limbs), in order to considerably increase the feeling of cooling and the comfort during the time-outs.

If applied to the neck it could be advantageously used for soothing the pain due to headache.

PRIOR ART

The need of cooling human body parts through a device of easy conception and easy positioning is particularly felt by persons who perform activities with a plentiful perspiration. For instance, in sports (such as tennis, basket, boxing) having frequent time-outs preceded by plentiful perspiration the athletes cool some body parts (nape of the neck, wrists, ankles) particularly stressed or shocked. In such cases they have to use rudimentary means as wet towels, bags filled with ice etc., which are not only uncomfortable to use and difficult to set on the affected surface, but do not even allow an efficient cooling of the part because of the defective adherence between said part and the cooling device.

Sometimes, in the treatment of some pathologies, as e.g. headaches, it is also suitable a strong cooling of human parts.

SUMMARY OF THE INVENTION

An object of the present invention is a device for the local cooling of human body parts. It basically consists of a sheath, of cooling means contained in the sheath and of a flexible leaf also contained in the sheath apt to adhere said sheath and said cooling means to the human part to cool.

The external part of the sheath could be advantageously made in a spongeous material in order to wipe the sweat, whereas the internal part could be made in a waterproof material in order to avoid the outgoing of the condensed water formed by the cooling. The leaf could be made in PVC, whereas the cooling means consists of a liquid contained in more or less stiff PVC containers.

LIST OF THE FIGURES

DETAILED DESCRIPTION OF THE INVENTION

Figure 1:
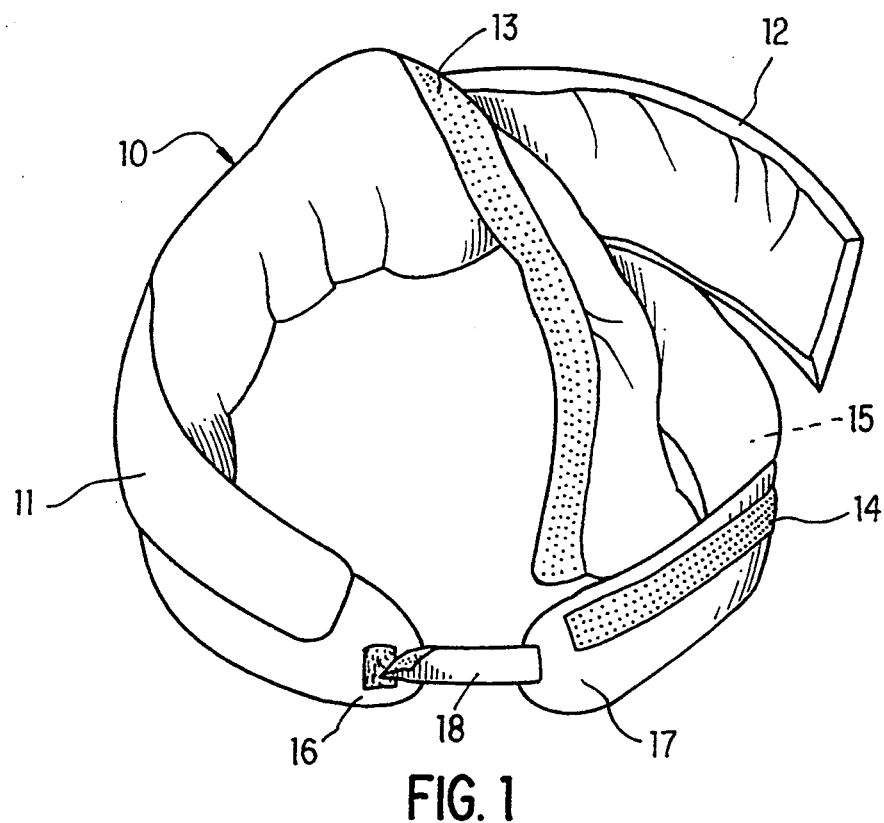
FIG. 1 represents a perspective overall view of the device according to the present invention.

FIG. 1 represents a perspective overall view of the cooling device 10 according to the present invention. For the reason of clarety the device 10 is represented "open" in order to show all of the elements present in said device 10.

Therefore, in the case shown in FIG. 1 it is possible to notice an elongate bag-shaped sheath 11 which presents on its upper side an opening allowing the introduction of the cooling means 12. It could consist of a cellophane bag, or of a bag made in an other more or less stiff PVC material filled with a cryogenic substance, e.g. with a substance used for the cooling of a picnic cooler fridge.

Either the cooling means 12 could be integral with the sheath 11, and in this case it is possible to cool together both elements, or it may be easily extractable from the sheath 11 in order to be cooled in a separate freezer not shown in FIG. 1. In the latter case the cooling means 12 has to have a shape similar to that of sheath 11 in order to ease the introduction of the cooling means 11 after the cooling operation.

As shown in FIG. 1 the opening of sheath 11 is closed by adhesive strips 13 and 14, but it is obviously possible to use any equivalent shutting means as For instance a zipper or clips.

The sheath 11 is in any material, e.g. in a spongeous fabric in order to efficiently wipe the sweat. It is possible to use a waterproof fabric in order to avoid the outgoing of the condensed water formed in the inner side; the use of a fabric with an external spongeous layer and an internal waterproof layer is particularly advantageous.

Figure 2:
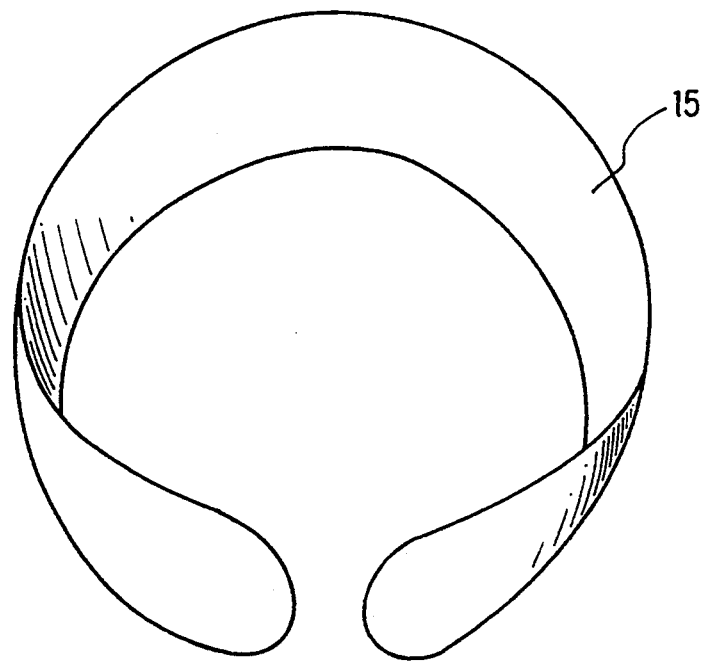
FIG. 2 represents a perspective overall view of a particular of FIG. 1.

Advantageously, in the internal side of the elongate bag-shaped sheath 11 it is also contained a flexible leaf 15, not shown in FIG. 1 because covered with an internal lining, but represented in its integrity in FIG. 2. Said flexible leaf has the same length and width of sheath 11 and allows the perfect adherence of said sheath 11 on the human body part which has to be cooled through the cooling means 12.

The working of the device 10 according to the present invention is the following:

1) In case the cooling means 12 is extractable from the sheath 11 the user puts said cooling means 12 previously cooled apart in said sheath 11;
2) the user closes the sheath 11 through the adhesive strips 13, 14;
3) afterwards the user deforms the flexible leaf 15 working as a rib in order to introduce the part which has to be cooled (neck, wrist, ankles or other articulations) in the internal side of the ring formed by the whole device 10. Because of the elasticity of the flexible leaf 15 working as a rib the device 10 in its totality comes back to its initial position thus adhering the internal part of the sheath 11 on the body part which has to be treated.

According to the particular requirements of the user, for instance to increase the adherence, tops 16, 17 of the device 10 could be provided with shuting means 18.

It is obvious that remaining in the scope of the present invention it is possible to imagine variations of the foresaid device.

We claim:

1. Device for the local cooling of a human body part comprising:
    a) a sheath having two ends;
    b) cooling means for cooling a body part contained in said sheath; and
    c) a flexible leaf comprised of resilient plastic contained in said sheath and having an elastic construction for urging opposite ends of the leaf toward one another, said ends of said flexible leaf urging the ends of said sheath together for wrapping the cooling means around a body part.

2. Device according to claim 1, wherein said cooling means is extractable from said sheath.

3. Device according to claim 2, wherein said sheath is provided with means for closing said sheath about the cooling means and flexible leaf.

4. Device according to claim 3, wherein said means for closing is a plurality of adhesive strips.

5. Device according to claim 3, wherein said means for closing is a zipper.

6. Device according to claim 3, wherein said means for closing is a plurality of clips.

7. Device according to claim 1, wherein said sheath is an absorbent material.

8. Device according to claim 1, wherein said cooling means is a substantially stiff bag filled with a cryogenic liquid.

9. Device according to claim 1, wherein said flexible leaf is comprised of PVC.

10. Device according to claim 1, further comprising means for holding the two ends of said sheath together.

11. Device according to claim 1, wherein said sheath is a waterproof material.

12. Device according to claim 1 wherein the inner side of said sheath is waterproof and the outer side of said sheath is absorbent.

* * * * *